United States Patent [19]

Ockert

[11] Patent Number: 5,376,662
[45] Date of Patent: Dec. 27, 1994

[54] METHOD OF ATTENUATING NERVE INJURY INDUCED PAIN

[76] Inventor: David M. Ockert, 860 United Nations Plz., 20F, New York, N.Y. 10017

[21] Appl. No.: 163,930

[22] Filed: Dec. 8, 1993

[51] Int. Cl.⁵ .......................................... A61K 31/485
[52] U.S. Cl. ..................................................... 514/282
[58] Field of Search ............................................ 514/282

[56] References Cited

U.S. PATENT DOCUMENTS

| | | |
|---|---|---|
| 4,105,659 | 8/1978 | Archer . |
| 4,582,835 | 4/1986 | Lewis et al. . |
| 4,668,685 | 5/1987 | Shami . |
| 4,673,679 | 6/1987 | Aungst et al. . |
| 4,722,928 | 2/1988 | Boswell et al. . |
| 4,753,635 | 6/1988 | Sagen et al. . |
| 4,760,069 | 7/1988 | Rzeszotarski et al. . |
| 4,769,372 | 9/1988 | Kreek . |
| 4,785,000 | 11/1988 | Kreek et al. . |
| 4,857,533 | 8/1989 | Sherman et al. . |
| 4,863,928 | 9/1989 | Atkinson et al. . |
| 4,888,346 | 12/1989 | Bihari et al. . |
| 4,889,860 | 12/1989 | Rzeszotarski et al. . |
| 4,990,617 | 2/1991 | Boswell et al. . |
| 5,013,739 | 5/1991 | Bihari et al. . |

OTHER PUBLICATIONS

"A Randomized, Controlled Trail of Methylprednisolone or Naloxone in the Treatment of Acute Spinal--Cord Injury", vol. 322, New Eng. J. Med., (May 1990), pp. 1405-1411, Bracken et al.

"Opiate-Receptor Antagonist Nalmefene Improves Neurological Recovery after Traumatic Spinal Cord Injury in Rates through a Central Mechanism", vol. 245, J. Pharmacology & Experimental Therapeutics, 742-48 (1988), Faden et al.

"111-Prostaglandin Hyperalgesia: Relevance of the Peripheral Effect for the Analgesic Action of Opioid-Antagonists", Prostaglandins, Aug. 1979, vol. 18, No. 2, pp. 201-208, Ferreira et al.

"Site of Analgesic Action of Aspirin-like Drugs and Opioids", In Mechanisms of Pain and Analgesic Compounds, New York: Raven Press pp. 309-321, Ferreira, 1979.

"Endogenous Opiates and Nociception: A Possible Functional Role in Both Pain Inhibition and Detection as Revealed by Intrathecal Naloxone", Neuroscience Letters, vol. 24 (1981) pp. 161-164, Dickenson et al.

"Effect of Naloxone Upon Diffuse Noxious Inhibitory Controls (DNIC) in the Rat", Brain Research vol. 240 (1981) 387-402, Le Bars et al.

"Reaction Thresholds to Pressure in Edematous Hind-paws of Rates and Responses to Analgesic Drugs", The Journal of Pharmacology and Experimental Therapeutics vol. 150, No. 1, pp. 165-171 Winter et al.

"Analgesia Produced by Low Doses of the Opiate Antagonist Naloxone in Arthritic Rats is Reduced in Morphine-Tolerant Animals", Brian Research, vol. 371 (1986), pp. 37-41 Kayser et al.

"Naloxone dose dependently produces analgesia and hyperalgesia in postoperative pain", Nature, vol. 278, (1979), pp. 740-741, Levine et al.

"Local Inhibition of Inflammatory Pain by Naloxone and its N-Methyl Quaternary Analogue," European Journal of Pharmacology, vol. 96, pp. 277-283, Rios et al., 1983.

(List continued on next page.)

Primary Examiner—Johann Richter
Assistant Examiner—Michael B. Hydorn
Attorney, Agent, or Firm—Price, Heneveld, Cooper, DeWitt & Litton

[57] ABSTRACT

The specification discloses a method of treating a human or animal patient suffering from a pain syndrome secondary to nerve injury comprising daily administration to such patient of from about 0.4 milligrams to about 2.0 milligrams of the opiate-receptor antagonist naloxone for a treatment period of from around 3 months to around 12 months, depending upon the patient's needs. Delivery is preferably at or near the nerve injury site by a number of conventional injection methods.

20 Claims, No Drawings

OTHER PUBLICATIONS

"Analgesia and hyperalgesia produced in the rat by intrathecal naloxone", Brain Research, vol. 189 (1980), pp. 593–597, Woolf.

"Behavorial evidence for a bidirectional effect of systemic naloxone in a model of experimental neuropathy in the rat", Brain Research, vol. 494 (1989), pp. 276–384, Attal et al.

"Behavioural and electrophysiological studies on the paradoxial antinociceptive effects of an extremely low dose of naloxone in an animal model of acute and localized inflammation", Exp Brain Res (1988) pp. 402–410 Kayser et al.

"II-Prostaglandin Hyperalgesia: The Peripheral Analgesic Activity of Morphine, Enkephalins and Opioid Antagonists", Prostaglandins, vol. 18, pp. 191–200, Ferreira et al. 1979.

"I-Prostaglandin Hyperalgesia, A cAMP/$CA^{2+}$ Dependent Process", Prostaglandins, vol. 18, No. 2 (1979), pp. 179–190, Ferreira et al.

"Drug Interaction in the Field of Analgesic Drugs", Proceedings of the Royal Society of Medicine, vol. 58, pp. 978–983, Lasagne, 1978.

"Naloxone alters pain perception and somatosensory evoked potentials in normal subjects", Nature, vol. 270 (1977), pp. 620–622, Buchsbaum et al.

"Antinociceptive Activity of Narcotic Agonist and Partial Agonist Analgesics and other Agents in the Tail–Immersion Test in Mice and Rats", Neuropharmacology, vol. 15 (1976), pp. 683–688, Sewell et al.

"Inhibition of Inflammatory Pain by Naloxone and its N Methyl Quaternary Analogue", Life Sciences, vol. 31 (1982), pp. 1209–1212, Rios et al.

"Dose-dependent analgesic and hyperalgesic effects of systemic naloxone in arthritic rats", Brain Research, vol. 226 (1981) pp. 344–348, Kayser et al.

"Opioid and Nonopioid Mechanism May Contribute to Dynorphin's Pathophysiological Actions in Spinal Cord Injury", Annals of Neurology, vol. 27, No. 1 (1990), pp. 67–74, Faden.

"Dynorphin A–(1–17) Induces Alterations in Free Fatty Acids, Excitatory Amino Acids, and Motor Function Through An Opiate-Receptor-Mediated Mechanism", The Journal of Neuroscience (1990), 10(12), pp. 3793–3800, Bakshi et al.

"Methylprednisolone or naloxone treatment after acute spinal cord injury: 1-year follow-up data", J. Neurosurg vol. 76 pp. 23–31 (1992), Bracken et al.

METHOD OF ATTENUATING NERVE INJURY INDUCED PAIN

BACKGROUND OF THE INVENTION

Frequently, nerve injuries result in severe and lingering complications such as back pain, peripheral neuropathy, neck pain, carpal tunnel syndrome, and the like. One of these complications is persistent and debilitating nerve injury induced pain syndrome. Typically, this pain manifests itself through severe discomfort, peripheral numbness, a decreased range of bodily motion, and decreased muscular strength. Due to these symptoms, pain syndrome associated with nerve injury can disrupt one's ability to function adequately at work or even fulfill social obligations.

Present clinical treatment methods for pain syndrome associated with nerve injury are numerous and varied. Included among them: over-the-counter medications such as aspirin, acetaminophen, and other non-steroidal anti-inflammatory agents; prescription medications which include narcotics such as morphine and Demerol, steroids, and local injections of nerve blockers like lidocaine or xylocaine. Other interventions include the use of serotonin-specific reuptake inhibitors, which include fluoxetine, peroxitine and sertraline. Still other treatments include non-pharmacological interventions such as physical therapy, spine manipulation, therapeutic massage, and, in specially severe cases, even spinal cord surgery.

Unfortunately, the efficacy of these treatments is limited to certain symptoms for subgroups of patients. For some patients a given method may provide modest relief from pain, but the majority of patients continue to experience disabling pain in spite of these treatments. Given both the limited benefits of present clinical methodology and the number of individuals who suffer from pain associated with nerve injury, it is easy to see why nerve injury induced pain syndrome represent expensive and debilitating disorders that challenge the current health care system.

Some have experimented with the use of nalmefene and naloxone in treating spinal cord injuries. L & I. Faden et al., *Opiate-Receptor Antagonist Nalmefene Improves Neurological Recovery after Traumatic Spinal Cord Injury in Rats through a Central Mechanism*, 245 J. Pharmacology & Experimental Therapeutics, 742–48 (1988). For example, Faden and colleagues showed that the opiate-receptor antagonist nalmefene was 100 times more potent than naloxone in promoting the recovery of motor skills, such as walking ability, in rats following spinal cord injury. A large scale study in humans shows that naloxone did not statistically reduce tissue damage at or near the site of spinal cord injury. Michael Bracken et al., *A Randomized, Controlled Trial of Methylprednisolone or Naloxone in the Treatment of Acute Spinal-Cord Injury*, Vol. 322, New Eng. J. Med. (1990).

Naloxone is currently FDA approved for the treatment of respiratory depression secondary to opiate overdose. Naloxone is also used to diagnose opiate dependence. While naloxone blocks the high associated with opiates, its short half-life in vivo, typically between 30 and 81 minutes (*Remington's Pharmaceutical Sciences*, 17th Edition), severely limits its value by requiring multiple doses for effective treatment of opiate dependence. Opiate-receptor antagonists with greater half-lives, e.g., naltrexone which can be taken orally, are therefore more clinically attractive for the treatment of opiate dependence and have received FDA approval for this use.

SUMMARY OF THE INVENTION

In the present invention, it has been surprisingly discovered that treatment with naloxone yields relief from nerve injury induced pain after the drug has been substantially metabolized. In the method of treatment of the present invention, individuals suffering from pain brought on by nerve injury are given an effective dose of the opiate-receptor antagonist naloxone from one to two times daily, via a clinically acceptable delivery method at or near the site of the individual's nerve injury. In spite of the short in vivo half life of naloxone, this procedure leads to pain relief within one hour, and relief continues for an additional 12 hours. Following discontinuation of a regular treatment schedule, one surprisingly experiences relief from pain at least for several days, sometimes weeks or even months.

These and other objects, advantages, and features of the present invention will be more fully understood and appreciated by reference to the written specification.

DESCRIPTION OF THE PREFERRED EMBODIMENT

The method of the present invention consists of the daily administration to human or animal patients suffering from a nerve injury induced pain syndrome, such as sciatica (back pain), neck pain, peripheral neuropathy, and carpal tunnel syndrome or the like, of from about 0.4 to about 2.0 milligrams of naloxone. Given the variability of pain and its symptoms in any given patient, this "typical" dosage may have to be repeated on a daily basis. Since naloxone has limited bioavailability and effectiveness when administered orally, any one of a number of injection methods, including intramuscular, intravenous, subcutaneous, and intradermal, are preferred. In addition, administration routes such as the subcutaneous implantation of naloxone-containing microcapsules or a transdermal patch system are also contemplated. All of these indicated delivery routes lend themselves to the local administration of naloxone at or near the nerve trauma site. Since local rather than systemic administration of naloxone has proven more effective in the treatment of pain, the former administration route is preferred in the treatment method of the present invention.

As used herein, the term "pain syndrome" or "nerve injury induced pain" refers to debilitating pain and its attendant symptoms such as a limited range of bodily motion, decreased muscular strength, numbness, parethesia and dysesthesia and the like, caused by nerve injury. This is meant to include both peripheral nerve injury, as well as central nerve injury, such as is associated with spinal cord injury.

By one preferred method, that involving some form of local injection, the effective dose of naloxone is administered to a patient once daily for anywhere from three to six months. Again, however, it may be necessary for a given patient to receive a second daily effective dose of naloxone and/or extend the total treatment period beyond the "typical" six months.

In addition to the foregoing treatment schedule, the preferred method of the present invention also contemplates the adjunctive use of other pharmacological and/or non-pharmacological treatments for patients with nerve injury induced pain syndrome. Of course, such adjunctive treatments will vary depending upon a particular patient's diagnosis. However, the typical course of treatment preferably includes some adjunctive treatment for the duration of the six-month period wherein the patient is likewise being treated with naloxone according to the present invention. Upon completion of naloxone treatment under the preferred method, patients will continue with adjunctive treatments such as anti-inflammatory agents, serotonin specific reuptake inhibitors (SSRI's) and/or physical therapy. In fact, the method of treatment of the present invention permits patients, as the symptoms of their nerve injury induced pain syndrome subside, to more easily engage in such non-pharmacological treatments as physical therapy.

Relief of pain occurs in about one hour and is continually enhanced over approximately the next three weeks. At the end of the preferred treatment method, usually somewhere about six months, the patient will be discontinued from naloxone administrations, with some patients remaining pain-free for an extended period of time after discontinuation.

The following example is illustrative of the method of the present invention. This example is not intended to limit or otherwise restrict the scope of the invention in any way and should not be construed as to limit dosages or methods of administration which are necessary to practice the invention.

EXAMPLE

A male patient, suffering from chronic, debilitating back pain as the result of an automobile accident, underwent several years of unsuccessful conventional treatment methods. This regimen included anti-inflammatory agents, back surgery, acupuncture, physical therapy, muscle relaxants, and anti-depressant medication. Due to the intolerable pain, the patient was ultimately prescribed narcotics. Though successful in the short term, the patient eventually became tolerant to the narcotic analgesia. To compensate, the narcotic dose was increased. However, unfortunate side effects including sedation, decreased concentration, and mental depression, limited the patient's ability to function and work in social situations almost as much as the debilitating back pain.

Following unsuccessful conventional treatment, the patient began a regimen of daily intramuscular injections of 0.4 milligrams naloxone. Approximately one-month later, the patient began receiving 0.4 milligrams of naloxone injected two times per day for a total dosage of 0.8 milligrams naloxone. As a result, the patient's back pain symptoms were significantly reduced.

About two months after beginning the regimen of 0.8 milligrams naloxone per day, the patient began a double-blind placebo-controlled experiment. The patient experienced reduction in pain symptoms and a reduction in numbness and dysesthesia with the naloxone injections but not with the placebo injections. As a result, the patient was once more put on an injection schedule of 0.4 milligrams of naloxone twice per day. In addition, the naloxone delivery method was altered to a subcutaneous injection near the site of the original nerve injury. It was discovered that this injection method offered the patient a maximal reduction in his pain symptoms.

Even when the use of naloxone was discontinued, the relief from pain continued. As symptoms returned several months later, the above treatment regimen was reinitiated with similar good results.

It is difficult to speculate as to the mechanism which leads to this surprising result. Clearly, naloxone is not only acting as an anti-inflammatory per se, since (1) the pain relief experienced is not coextensive with the very short in vivo life of naloxone and (2) one begins to experience substantial relief from pain only some time after the naloxone has been at least about 50% or more metabolized. Naloxone and other opiate-antagonists competitively antagonize both exogenous opiates (such as heroine or morphine) and endogenous opioids (such as B-endorphin, enkephalins, and dynorphin at both peripheral and central nerve opiate receptors). By competing with the natural pain relievers, one would expect that the administration of opiate antagonists such as naloxone would increase pain. Surprisingly, however, naloxone apparently triggers some mechanism in the body which actually results in relief of pain some time after administration, and continuing for a period of time beyond the period of administration.

Of course, it is understood that the above is merely a preferred embodiment of the invention, and that various other embodiments as well as many changes and alterations, apparent to those skilled in the art, may be made without departing from the spirit and broader aspects of the invention as defined in the claims.

The embodiments of the invention in which an exclusive property or privilege is claimed are defined as follows:

1. A method of treating a human or animal patient suffering from a nerve injury induced pain syndrome comprising the daily administration to the patient of from about 0.4 milligrams to about 2.0 milligrams of the opiate-receptor antagonist naloxone.

2. The method of claim 1 wherein said pain syndrome is characterized by debilitating, persistent pain, decreased muscular strength, numbness, parethesias and dysesthesias.

3. The method of claim 1 wherein said naloxone is administered at or near the site of the patient's nerve injury.

4. The method of claim 3 wherein said naloxone is administered to the patient by intramuscular injection.

5. The method of claim 3 wherein said naloxone is administered to the patient by intravenous injection.

6. The method of claim 3 wherein said naloxone is administered to the patient by subcutaneous implantation.

7. The method of claim 3 wherein said naloxone is administered to the patient by intradermal application.

8. The method of claim 1 wherein said administration of said naloxone to the patient is made from 1 to 2 times daily for a period of anywhere from about 3 to about 12 months.

9. The method of claim 8 wherein said naloxone is administered at or near the site of the patient's nerve injury.

10. The method of claim 9 wherein said naloxone is administered to the patient by intramuscular injection.

11. The method of claim 9 wherein said naloxone is administered to the patient by intravenous injection.

12. The method of claim 9 wherein said naloxone is administered to the patient by subcutaneous implantation.

13. The method of claim 9 wherein said naloxone is administered to the patient by intradermal application.

14. A method of treating a human or animal patient suffering from nerve injury induced pain syndrome comprising the daily administration to the patient of from about 0.4 milligrams to about 2.0 milligrams of the opiate-receptor antagonist naloxone, and concurrently treating the patient with one or more conventional pharmacological or non-pharmacological treatments.

15. The method of claim 14 wherein said naloxone is administered at or near the site of the patient's nerve trauma.

16. The method of claim 15 wherein said naloxone is administered to the patient by intramuscular injection.

17. The method of claim 15 wherein said naloxone is administered to the patient by intravenous injection.

18. The method of claim 15 wherein said naloxone is administered to the patient by subcutaneous implantation.

19. The method of claim 15 wherein said naloxone is administered to the patient by intradermal application.

20. The method of claim 15 wherein said administration of said naloxone to the patient is made from 1 to 2 times daily for a period of anywhere from about 3 to about 12 months.

* * * * *